United States Patent
Morrison, III et al.

(10) Patent No.: US 12,042,528 B2
(45) Date of Patent: Jul. 23, 2024

(54) HYALURONIDASE FOR THE PREVENTION, TREATMENT, REDUCTION AND/OR ABOLISHMENT OF CEREBRAL EDEMA AND INTRACRANIAL PRESSURE

(71) Applicant: The Trustees of Columbia University in the City of New York, New York, NY (US)

(72) Inventors: Barclay Morrison, III, New York, NY (US); Steve Kernie, Larchmont, NY (US); Patricia Walker, Richmond, VA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 401 days.

(21) Appl. No.: 16/957,817

(22) PCT Filed: Nov. 28, 2018

(86) PCT No.: PCT/US2018/062846
§ 371 (c)(1),
(2) Date: Jun. 25, 2020

(87) PCT Pub. No.: WO2019/133166
PCT Pub. Date: Jul. 4, 2019

(65) Prior Publication Data
US 2021/0369819 A1    Dec. 2, 2021

Related U.S. Application Data

(60) Provisional application No. 62/611,605, filed on Dec. 29, 2017.

(51) Int. Cl.
A61K 38/47    (2006.01)
A61P 7/10    (2006.01)

(52) U.S. Cl.
CPC ............... *A61K 38/47* (2013.01); *A61P 7/10* (2018.01); *C12Y 302/01035* (2013.01)

(58) Field of Classification Search
CPC .................... A61K 38/243; A61K 31/1787
See application file for complete search history.

(56) References Cited

U.S. PATENT DOCUMENTS

| | | |
|---|---|---|
| 6,193,963 B1 | 2/2001 | Stern et al. |
| 8,765,685 B2 | 7/2014 | Bookbinder et al. |
| 2010/0003238 A1 | 1/2010 | Frost et al. |
| 2012/0251620 A1 | 10/2012 | Bookbinder et al. |
| 2014/0323930 A1 | 10/2014 | Edwards |

OTHER PUBLICATIONS

Nekoroski et al., "A recombinant human hyaluronidase sustained release gel for the treatment of post-surgical edema", International Journal of Dermatology, vol. 53, No. 6, pp. 777-785 (2014).*
Washington et al., "Hyaluronidase Reduces Edema After Experimental Traumatic Brain Injury In Mice: Support For The Fixed-Charge Density Hypothesis", Journal of Neurotrauma, vol. 33, Abstract No. PSB-254 (Jul. 2016).*
Pimentel et al., "Local Injection of Hyaluronidase in Increasing Skin Flap Survival: An Experimental Study", Brazilian Journal of Plastic Surgery, vol. 14, No. 1, pp. 49-55 (1999).*
Bhattacharya et al. (Jan. 17, 1989) Hyaluronan affects extravascular water in lungs of unanesthetized rabbits. Journal of Applied Physiology 66:2595-2599.
Blaiss et al. (Mar. 30, 2011) Temporally specified genetic ablation of neurogenesis impairs cognitive recovery following brain injury. Journal of Neuroscience 31:4906-16.
Elkin et al. (Feb. 13, 2010) Fixed negative charge and the Donnan effect: a description of the driving forces associated with brain tissue swelling and oedema. Philosophical Transactions Series A, Mathematical, Physical, and Engineering sciences 368:585-603.
Elkin et al. (2011) Chondroitinase ABC reduces brain tissue swelling in Vitro. Journal of Neurotrauma 282277-2285.
Finan et al. (Mar. 12, 2016) Intracerebroventricular administration of chondroitinase ABC reduces acute edema after traumatic brain injury in mice. BMC Research Notes 9:160.
Hunger et al. (Jul. 2012) Hydration dynamics of hyaluronan and dextran. Biophysical Journal 103:L10-12.
Hylin et al. (Feb. 6, 2013) Disruption of the perineuronal net in the hippocampus or medial prefrontal cortex impairs fear conditioning. Learning and Memory 20:267-273.
Kochlamazashvili et al. (Jul. 15, 2010) The extracellular matrix molecule hyaluronic acid regulates hippocampal synaptic plasticity by modulating postsynaptic L-type Ca(2+) channels. Neuron 67:116-128.
Lang et al. (Apr. 2, 2014) Is the Donnan effect sufficient to explain swelling in brain tissue slices? Journal of the Royal Society, Interface 11:20140123.

(Continued)

*Primary Examiner* — Kevin E Weddington
(74) *Attorney, Agent, or Firm* — Leason Ellis LLP

(57) ABSTRACT

The current invention is a method of treating, preventing, reducing and/or abolishing edema and/or intracranial pressure in a subject by the administration of hyaluronidase. The edema in the brain and intracranial pressure can be the result of a traumatic event, disease or condition including but not limited to a traumatic brain injury, a stroke, a brain tumor, and post-operative swelling.

16 Claims, 7 Drawing Sheets

(56) References Cited

OTHER PUBLICATIONS

Marmarou et al. (Aug. 2000) Contribution of edema and cerebral blood volume to traumatic brain swelling in head-injured patients. Journal of Neurosurgery 93:183-193.

Marmarou et al. (May 2006) Predominance of cellular edema in traumatic brain swelling in patients with severe head injuries. Journal of Neurosurgery 104:720-730.

Nettelbladt et al. (Jul. 14, 1989) Lung accumulation of hyaluronan parallels pulmonary edema in experimental alveolitis. The American Journal of Physiology 139:682-87.

Thomas et al. (Mar. 8, 2006) In vivo measurement of the longitudinal relaxation time of arterial blood (T1a) in the mouse using a pulsed arterial spin labeling approach. Magnetic Resonance in Medicine 55:943-947.

Tofts et al. (1991) Measurement of the blood-brain barrier permeability and leakage space using dynamic MR imaging. 1. Fundamental concepts. Magnetic Resonance in Medicine 17:357-367.

Upadhyay (Jul. 20, 2014) Drug delivery Systems, CNS Protection, and the Blood Brain Barrier. BioMed Research International 2014: ID 869269

Vlachos et aL. (Sep. 21, 2010) Permeability assessment of the focused ultrasound-induced blood-brain barrier opening using dynamic contrast-enhanced MRI. Physics in Medicine and Biology 55:5451-5466.

Waldenstrom et al. (Nov. 1991) Accumulation of hyaluronan and tissue edema in experimental myocardial infarction. The Journal of Clinical Investigation 88:1622-1628.

Winkler et al. (Oct. 2016) Cerebral Edema in Traumatic Brain Injury: Pathophysiology and Prospective Therapeutic Targets. Neurosurgery Clinics of North America 27:473-488.

Yu et al. (Nov. 26, 2008) Traumatic brain injury-induced hippocampal neurogenesis requires activation of early nestin-expressing progenitors. The Journal of Neuroscience : the Official Journal of the Society for Neuroscience 28:12901-12912.

Zweckberger et al. (Jul. 25, 2006) Effect of early and delayed decompressive craniectomy on secondary brain damage after controlled cortical impact in mice. Journal of Neurotrauma 23:1083-1093.

Zhu, Jiajia et al., "Glycocalyx degradation leads to blood-brain barrier dysfunction and brain edema after asphyxia cardiac arrest in rats", J Cereb Blood Flow Metab. Nov. 2018;38(11):1979-1992. doi: 10.1177/0271678X17726062. Epub Aug. 21, 2017.

Hall, Aaron A., "Repeated Low Intensity Blast Exposure Is Associated with Damaged Endothelial Glycocalyx and Downstream Behavioral Deficits", Front Behav Neurosci. Jun. 9, 2017;11:104. doi: 10.3389/fnbeh.2017.00104. eCollection 2017.

Raghavan, Preeti et al., "Human Recombinant Hyaluronidase Injections For Upper Limb Muscle Stiffness in Individuals With Cerebral Injury: A Case Series", EBioMedicine. Jul. 2016;9:306-313. doi: 10.1016/j.ebiom.2016.05.014.

* cited by examiner

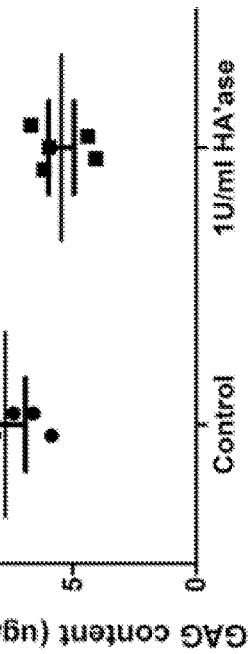
Figure 1A Cortical explant edema
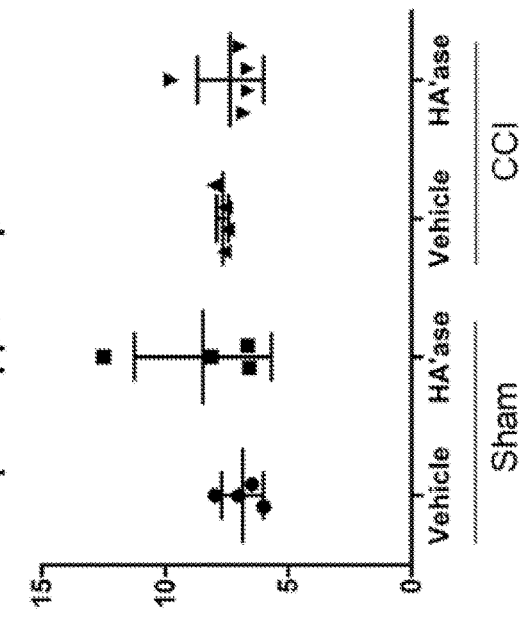
Figure 1B Cortical explant FCD
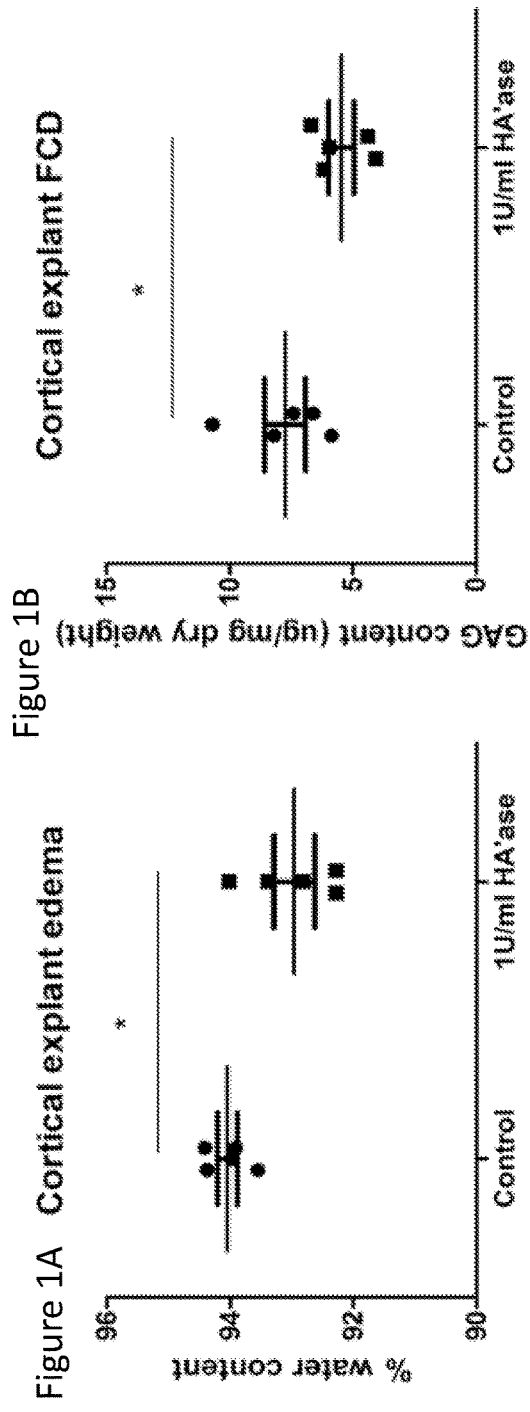
Figure 1C Ipsi. hippocampus edema
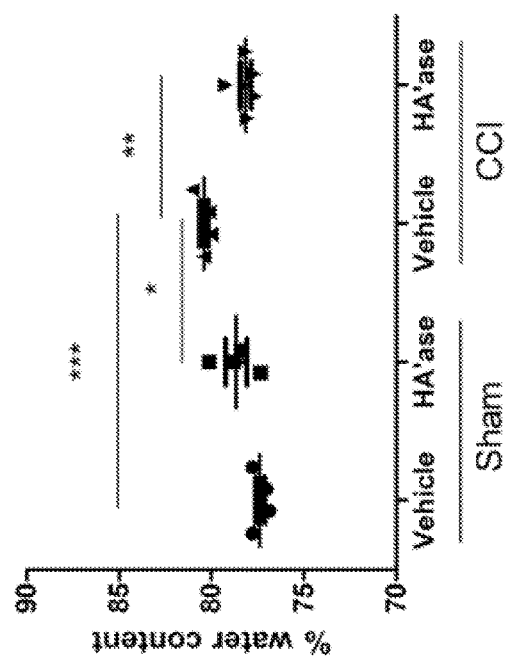
Figure 1D Ipsi. hippocampus FCD

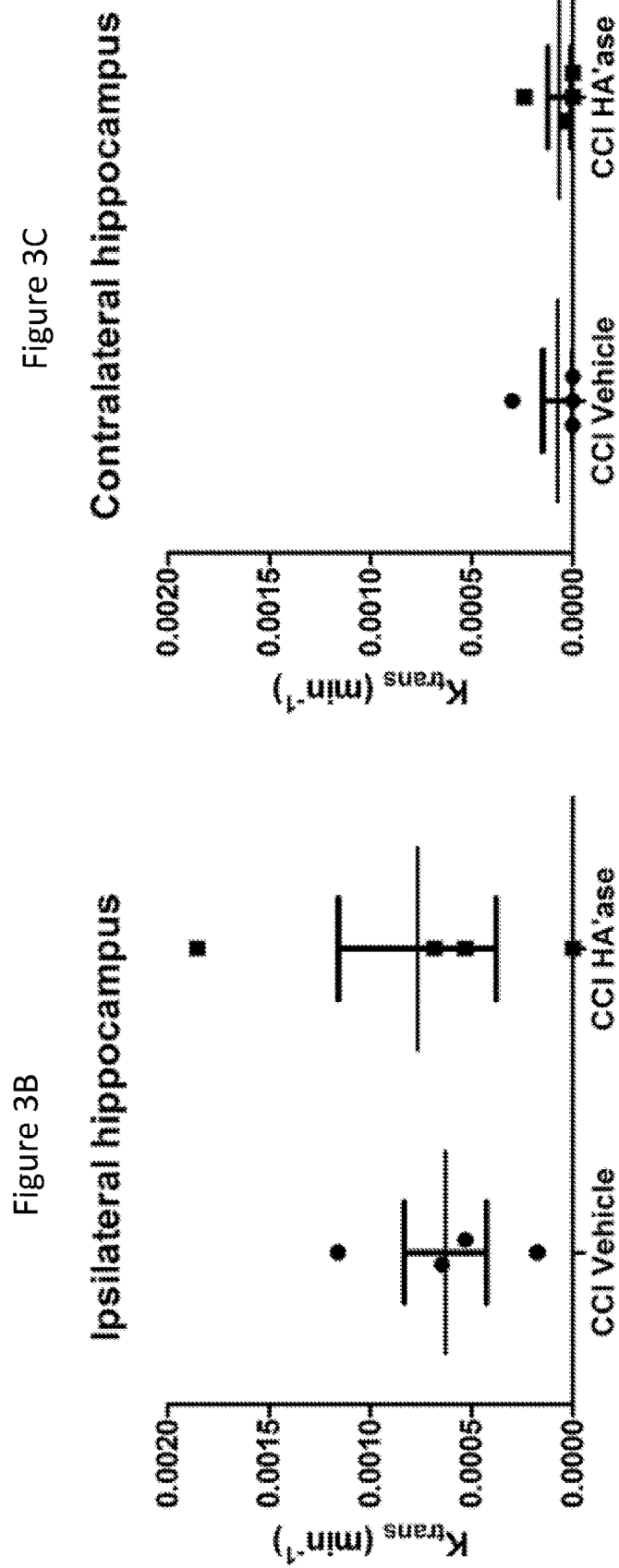

HYALURONIDASE FOR THE PREVENTION, TREATMENT, REDUCTION AND/OR ABOLISHMENT OF CEREBRAL EDEMA AND INTRACRANIAL PRESSURE

CROSS REFERENCE TO RELATED APPLICATION

The present application is a U.S. National Phase Application under 35 U.S.C. § 371 of International Patent Application Serial No. PCT/US2018/062846, filed Nov. 28, 2018, which claims priority to U.S. Patent Application Ser. No. 62/611,605, filed Dec. 29, 2017, each of which are hereby incorporated by reference as if expressly set forth in its entirety herein.

FIELD OF THE INVENTION

This invention is in the field of preventing, treating, reducing and/or abolishing cerebral edema and the subsequent intracranial pressure caused therein, by the administration of hyaluronidase. The cerebral edema can be caused by any traumatic event, disease or condition including but not limited to a traumatic brain injury, a stroke, a brain tumor, and post-operative swelling.

BACKGROUND OF THE INVENTION

Cerebral edema following traumatic brain injury (TBI) is associated with poor outcome and increased mortality, as swelling of the brain within the rigid skull can increase intracranial pressure (ICP) and result in coma, brain herniation and death (Tucker et al., 2017). While strategies to manage elevated ICP following severe TBI include administration of the hyperosmotic agents, mannitol and hypertonic saline, hyperventilation, barbiturate coma, and decompressive craniectomy, each of these interventions are associated with adverse effects, and their efficacy is still a major topic of investigation and debate (Stocchetti and Maas, 2014).

A major obstacle to developing targeted treatments for elevated ICP is a limited understanding of the mechanisms underlying post-traumatic formation of edema in the brain. Cerebral edema with a net increase in brain water content leads to an increase in brain volume. Marmarou et al. identified that edema drives brain swelling in human TBI, as opposed to vascular engorgement and an increase in cerebral blood volume (Marmarou et al., 2000). There are two major types of brain edema: vasogenic edema and cytotoxic edema. Vasogenic edema is an increase in water in the extracellular space due to an osmotic gradient generated by extravasation of plasma-derived solutes from the vasculature as a result of blood brain barrier (BBB) permeability or breakdown. Cytotoxic edema, or cell swelling, is an increase in water in the intracellular compartment in response to accumulation of osmotically active solutes within the cell.

Regardless of the type of edema, the primary issue is a net accumulation of water in the tissue and an inability to equilibrate. Preclinical studies have identified a number of cellular and molecular mechanisms that contribute to the development of cytotoxic and vasogenic edema, including: excitotoxicity due to excessive glutamate release; mitochondrial dysfunction; ion pump failure; degradation of BBB components by matrix metalloproteinases; inflammation-induced release of vasoactive agents; insertion of aquaporin 4 water channels into the cell membrane allowing bi-directional transport of water; and mechanical injury to the vasculature and tissue (Donkin and Vink, 2010; Winkler et al., 2016).

Previous studies using triphasic mixture theory to model the swelling behavior of brain tissue have shown that dead brain tissue swells as described by the Gibbs-Donnan effect (Elkin et al., 2010, 2011; Lang et al., 2014; Angeli and Stylianopoulos, 2017). The Gibbs-Donnan effect describes the tendency of a porous, negatively-charged matrix to generate an osmotic gradient that attracts positive ions and water into the matrix, causing the matrix to swell. In the brain, glycosaminoglycans (GAGs) such as chondroitin sulfate proteoglycan, are immobilized, negatively-charged matrix-molecules that contribute to the fixed charge density (FCD) of the tissue. Enzymatically degrading chondroitin sulfate both in vitro (Elkin et al., 2011) and in vivo in a mouse model of TBI (Finan et al., 2016) reduced tissue swelling, identifying the FCD as a potential osmotic agent of edema.

Increased ICP is a common and serious complication of TBI and is also associated with other brain related illness and traumatic events such as stroke, brain tumors, and post-operative swelling. Thus, there is an urgent need for therapeutic strategies that reduce ICP by directly targeting post-traumatic cerebral edema. As there are many FCD constituents in the brain, enzymatically targeting any may lead to an attenuation of edema after TBI. Hyaluronan is a large, negatively-charged extracellular matrix molecule that contributes to the FCD in the brain.

Herein it was demonstrated that intracerebroventricular (ICV) injection of hyaluronidase reduced edema in a mouse model of TBI and provided additional evidence to support the FCD hypothesis of edema.

SUMMARY OF THE INVENTION

Cerebral edema and subsequent increased intracranial pressure (ICP) are associated with mortality and poor outcome following traumatic brain injury (TBI). As shown herein, hyaluronidase (HA'ase), an enzyme that degrades the large, negatively-charged glycosaminoglycan hyaluronan, reduced brain fixed charged density (FCD) and edema.

Hyaluronidase reduced the water content and FCD of cortical explants in an in vitro swelling assay compared to control solution as measured by the wet-weight/dry-weight method and dimethymethylene blue assay. In vivo, intracerebroventricular (ICV) injection of hyaluronidase after controlled cortical impact (CCI) in mice reduced edema in the ipsilateral hippocampus at 24 hours compared to vehicle as measured by both the wet-weight/dry-weight method and T2-weighted magnetic resonance imaging (MRI). Dynamic contrast-enhanced MRI showed no adverse effects of hyaluronidase on the blood brain barrier (BBB), and hyaluronidase did not negatively affect the trajectory of functional recovery after CCI in the rotarod and Morris water maze tasks. These data demonstrated that targeting the FCD with hyaluronidase reduces edema both in vitro and in an in vivo mouse model of TBI.

Thus one embodiment of the current invention is a method of treating a traumatic brain injury in a subject in need thereof comprising administering to the subject a therapeutically effective amount of hyaluronidase.

A further embodiment of the current invention is a method of treating, preventing, reducing and/or abolishing edema and/or intracranial pressure following a traumatic brain injury in a subject in need thereof comprising administering to the subject a therapeutically effective amount of hyaluronidase.

Intracranial pressure and edema also arise from other conditions, disease and traumatic events including but not limited to stroke, brain tumors, and post-operative swelling. Thus, a further embodiment of the current invention is a method of treating, preventing, reducing and/or abolishing edema and/or intracranial pressure in a subject in need thereof comprising administering to the subject a therapeutically effective amount of hyaluronidase. In this embodiment, the subject is known or suspected of having edema in the brain and intracranial pressure resulting from a traumatic event, disease or condition other than a traumatic brain injury including but not limited to a stroke, a brain tumor, and post-operative swelling.

In some embodiments, the hyaluronidase can be administered immediately after the traumatic brain injury, traumatic event, disease or condition has occurred. In some embodiments, the hyaluronidase can be administered over a month after the traumatic brain injury, traumatic event, disease or condition has occurred. In some embodiments, the hyaluronidase can be administered to the subject as soon as edema in the brain tissue and/or intracranial pressure is known or suspected.

In some embodiments, the hyaluronidase can be administered directly into the brain via an intraventricular administration. In some embodiments, the hyaluronidase is administered intraparenchymaly (directly into the brain tissue). In some embodiments, the hyaluronidase can be administered using a method that allows the enzyme to cross the blood brain barrier to reach the brain tissue. Any method known in the art currently or later developed that allows compound and agents to cross the blood brain barrier can be used to administer the hyaluronidase into the brain tissue.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

FIG. 1: Hyaluronidase (HA'ase) reduced water content in vitro in a cortical explant swelling assay and in vivo following CCI injury in mice. FIG. 1A is a graph showing that the incubation in 1 U/ml HA'ase for 24 hours reduced the percent water content of explants compared to incubation in control solution (Gey's solution) as measured by the wet-weight/dry-weight method. FIG. 1B is a graph showing that the incubation in 1 U/ml HA'ase reduced GAG content compared to control solution as measured by the DMMB assay. $*p<0.05$, unpaired t-test; n=5/group. FIG. 1C is a graph showing that the percent water content in the ipsilateral hippocampus of vehicle-treated mice was increased at 24 hours after Controlled Cortical Impact (CCI) injury compared to sham-injured mice. Treatment with HA'ase reduced this observed increase in edema after CCI (n=4-5 mice/group). FIG. 1D shows that HA'ase treatment did not alter GAG content of the ipsilateral hippocampus in sham or CCI mice $*p<0.05$, $p<0.01$, $*p<0.001$; one-way ANOVA with Tukey's post hoc multiple comparisons.

FIG. 2: HA'ase treatment following CCI injury in mice reduced edema. FIGS. 2B and 2D—$*p<0.05$, $**p<0.01$ unpaired t-test. FIGS. 2C and 2E—$*p<0.05$, $**p<0.01$ one-way ANOVA with Tukey's post hoc multiple comparisons. n=4 mice/group.

FIG. 3: Hyaluronidase did not increase BBB permeability in the ipsilateral hippocampus after CCI. FIG. 3B is a graph showing the $K_{trans}$, a measure of blood brain barrier permeability, was no different between vehicle- and HA'ase-treated CCI mice (n.s.) in the ipsilateral hippocampus. FIG. 3C is a graph showing the $K_{trans}$ was no different between vehicle—and HA'ase-treated CCI mice (n.s.) in the contralateral hippocampus. Unpaired t-test. n=4 mice/group.

FIG. 4: Hyaluronidase treatment did not alter recovery of function after CCI injury.

DETAILED DESCRIPTION OF THE INVENTION

Figure 2A:
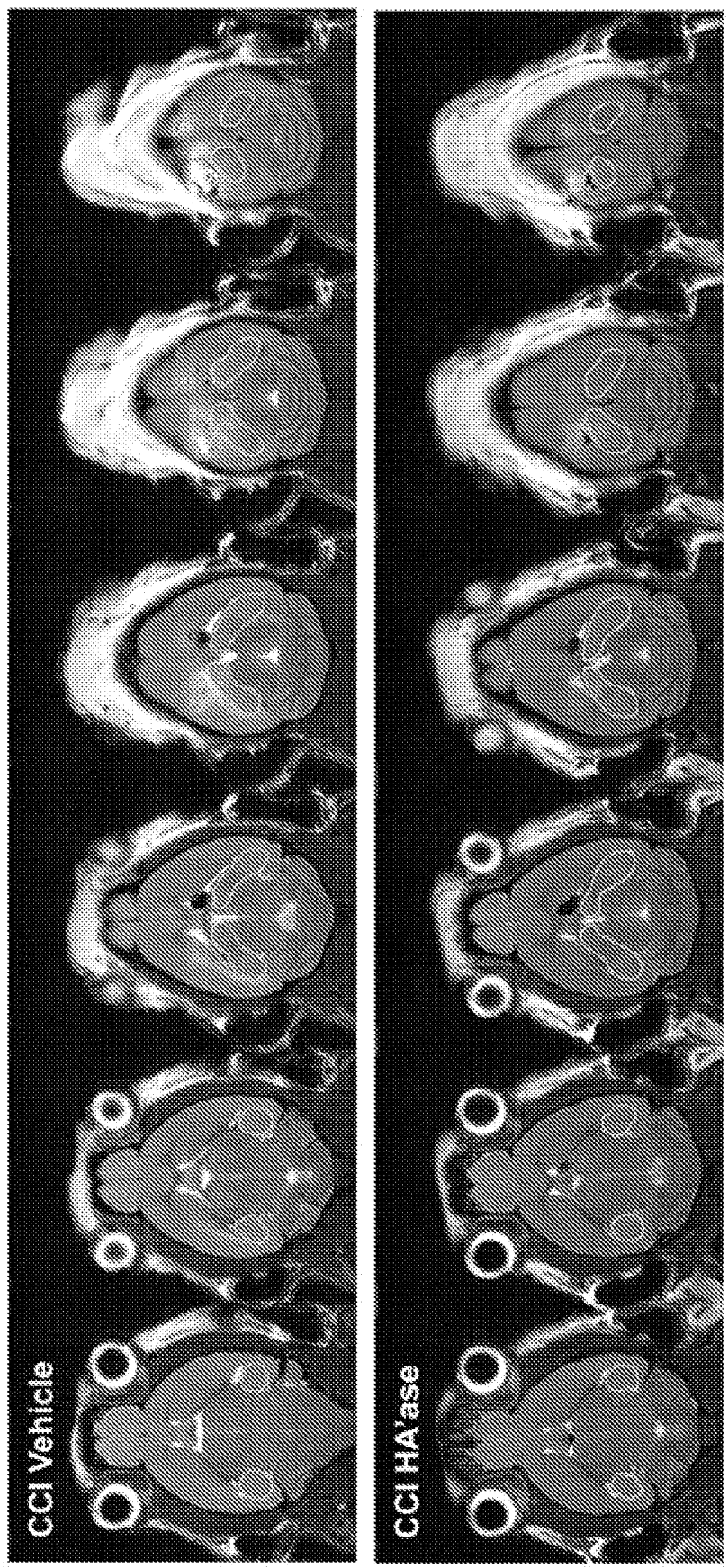
FIG. 2A are representative serial, axial T2-weighted MRI images from CCI vehicle (top images) and CCI HA'ase (bottom images) mice showing hyperintense regions indicative of edema at different levels of the hippocampus in the same animal

The present invention is a new and effective method of preventing, treating, reducing and/or abolishing cerebral edema and the resulting intracranial pressure by the administration of hyaluronidase.

Abbreviations

TBI—traumatic brain injury
ICP—intracranial pressure
BBB—blood brain barrier
GAG—glycosaminoglycans
FCD—fixed charge density
ICV—intracerebroventricular
HA'ase—hyaluronidase
CCI—controlled cortical impact
DMMB—1'9 dimethylmethylene blue
MRI—magnetic resonance imaging
DCE—dynamic contrast-enhanced
MWM—Morris water maze Definitions The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "injury" would refer to tissue or organ damage, and includes any alteration in tissue or organ structure, cell viability or function. As used herein, "injury" can include but is not limited to a traumatic brain injury.

The terms "treat", "treatment", and the like refer to a means to slow down, relieve, ameliorate, or alleviate the damage or injury to the tissues and/or organs or reverse the damage after its onset.

The terms "prevent", "prevention", and the like refer to acting prior to overt disease onset, to prevent the disease from developing or minimize the extent of the disease or slow its course of development.

The term "protect", "protection" and the like refer to a means to ameliorate the damage from the injury or stop the injury to the organ and/or tissue from occurring.

The term "subject" as used in this application means an animal with an immune system such as avians and mammals Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject.

The term "in need thereof" would be a subject known or suspected of having sustained an injury, in particular to the brain. It would also include a subject known or suspected of having edema in the brain and intracranial pressure (ICP) resulting from traumatic events other than an injury and would include but is not limited to stroke, a brain tumor, and post-operative swelling.

The phrase "therapeutically effective amount" is used herein to mean an amount sufficient to cause an improvement in a clinically significant condition in the subject, or delays or minimizes or mitigates one or more symptoms associated with the injury, or results in a desired beneficial change of physiology in the subject.

The phrase "pharmaceutically acceptable" as used herein refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Hyaluronidase Reduces Edema in Brain Tissue after a Traumatic Brain Injury (TBI) or Other Traumatic Event The fixed charge density (FCD) hypothesis of edema suggests that brain tissue swells according to the Gibbs-Donnan effect and that one of the contributing osmotic driving forces is the negative charge of the tissue (Elkin et al., 2010, 2011; Finan et al., 2016). Therefore, it was hypothesized that any negatively-charged molecule that contributes to the FCD, such as hyaluronan, could serve as a potential target for reducing edema. Shown herein, hyaluronidase reduced the percent water content of brain tissue in both an in vitro cortical explant swelling assay (Example 2) and an in vivo model of TBI in mice (Examples 3 and 4). These findings provide additional evidence that the FCD contributes to development of cerebral edema after experimental TBI and that enzymatically targeting the FCD can reduce edema.

In humans, intracranial pressure (ICP) increases exponentially in response to small increases in edema due to any cause including but not limited to TBI, stroke, a brain tumor and post-operative swelling. A 1% increase in brain water content in TBI patients is associated with ICP levels of 20 mmHg or higher (Marmarou et al., 2006), compared to normal ICP values of 10-15 mmHg (Stocchetti and Maas, 2014). As increased ICP is associated with deleterious effects including coma, brain herniation and death (Tucker et al., 2017), mitigating edema and ICP may be advantageous for patient survival. Unfortunately, therapeutic strategies that have shown promise in preclinical studies, such as steroids, have failed to demonstrate efficacy or improve outcome in clinical trials (Chakraborty et al., 2016).

Previous studies of edema using the CCI model in rodents have shown that edema peaks at 24 hours after injury with an increase in percent water content of approximately 1-3%

(Zweckberger et al., 2006). In contrast to edema, the time course of BBB breakdown after controlled cortical impact (CCI) is more variable between studies, and has been reported to be biphasic with a relative dip in permeability at 24 hours compared to earlier and later time points in both the ipsilateral cortex and hippocampus (Baskaya et al., 1997) as well as increased at 4, 8 and 24 hours after injury with the maximum at 24 hours (Zweckberger et al., 2006). As edema was the primary interest, edema and brain blood barrier (BBB) were evaluated at 24 hours after injury, during the expected peak of edema.

Similar to previous studies, as shown herein, CCI increased percent water content in the ipsilateral hippocampus by 3%, which was reduced to a 1% increase over sham mice by treatment of the CCI mice with hyaluronidase. (Example 3). Sequential T2-weighted MRI and T1-weighted MRI with contrast agent to quantify both edema and BBB permeability in the same animals indicated the presence of both edema in the brain and BBB opening at 24 hours after CCI. While it was not possible to determine whether this was the peak of BBB opening as it was only assessed at one time point, it is clear that there was BBB breakdown that could contribute to edema formation as accumulation of the MRI contrast agent was visible in the ipsilateral cortex around the injury site and the contralateral cortex at the site of ICV injection in both groups. However, Kt in the ipsilateral hippocampus was not different between vehicle- and hyaluronidase-treated CCI mice, and the low values suggest that a large increase in BBB permeability does not occur in the hippocampus, as further evidenced qualitatively by the lack of accumulation of contrast agent in this region. See Example 4.

In the in vitro cortical explant swelling assay, the FCD content of hyaluronidase-treated explants was reduced compared to that of controls, indicating enzyme activity and reduced FCD (Example 2). These findings were in agreement with previous in vitro studies showing that incubation of brain tissue slices in enzymes that reduced GAG content, including chondroitinase, heparinase and DNA'ase, reduced uptake of water and tissue swelling (Elkin et al., 2010, 2011). Together, these studies suggest a relationship between the FCD of tissue and water content, and that reducing the FCD of the tissue is a potential approach for reducing water content.

Chondroitinase was further shown to reduce brain edema following CCI in mice (Finan et al., 2016), but GAG content was not reported. Although hyaluronidase reduced GAG content in vitro in the present study, a change in GAG content was not observed in vivo in sham or CCI mice treated with hyaluronidase compared to vehicle (Examples 2 and 3). This lack of reduction may be related to the mechanism by which degradation of hyaluronan by hyaluronidase leads to a reduction in FCD and edema. Potential mechanisms include complete enzymatic degradation of hyaluronan by injected or endogenous hyaluronidases, clearance of hyaluronan degradation products via the liver or the lymph nodes, or mobilization and diffusion of previously fixed hyaluronan and hyaluronan-bound negative charges leading to restoration of ionic and osmotic equilibrium. The observed reduction in total tissue FCD in the in vitro assay (where mobilized charges could diffuse out into solution), and no change in total FCD in vivo (where equilibrium might have resulted from shifts of mobilized charges between intracellular and extracellular compartments and not from exiting the parenchyma) may suggest that hyaluronidase reduced tissue FCD through mobilization and diffusion of negative charges rather than by complete degradation and elimination. It is also important to note that the DMMB assay quantifies negative charges but does not detect or quantify hyaluronan directly.

Hyaluronan is composed of repeating disaccharides of glucoronic acid and N-acetylglucoasmine and can range in size from 2,000-25,000 disaccharides (Toole, 2004). Each disaccharide unit can bind and retain 10-15 molecules of water (Hunger et al., 2012) making hyaluronan a key component for tissue hydration. Increased levels of hyaluronan have been implicated in the development of edema in several conditions, including experimental myocardial infarction (Waldenstrom et al., 1991) and experimental pulmonary edema (Nettelbladt et al., 1989). Hyaluronan has also been shown to be directly related to extravascular water content in rabbit lungs, with hyaluronidase infusion decreasing lung water content (Bhattacharya et al., 1989).

BBB permeability was evaluated as hyaluronan is a component of brain endothelial surface glycocalyx and a potential concern could be that degrading a BBB component could increase permeability. However, intraventricular (ICV) administration of hyaluronidase did not exacerbate CCI-induced BBB permeability as shown with DCE MRI (Example 4).

Further, of the behavioral outcome measures that were assessed, the performance of hyaluronidase and vehicle-treated sham and CCI mice did not differ from that of each other or naïve mice, suggesting that any major potential off-target effects of hyaluronan degradation did not manifest as changes in motor function or hippocampal-dependent spatial learning and memory during the course of the testing period (Example 5). Previous studies have shown that injection of hyaluronidase (different from the one used in this study) into the hippocampus (Kochlamazashvili et al., 2010) or infusion of hyaluronidase plus chondroitinase into the hippocampus (Hylin et al., 2013) impaired fear conditioning, a hippocampal-dependent task. Here, ICV injection of hyaluronidase did not have deleterious effects on hippocampal function as evaluated by the Morris water maze.

Modes of Administration, Dosing and Timing of Administration

Hyaluronidase can be administered any time after a traumatic brain injury, another traumatic event or disease or condition that results or can result in edema in the brain and intracranial pressure has occurred.

In one embodiment, the hyaluronidase is administered immediately after the traumatic brain injury or traumatic event or disease or condition has occurred. In some embodiments, the hyaluronidase is administered within about one hour, two hours, five hours, 10 hours, 15 hours, 20 hours, up to 24 hours of the injury or traumatic event or disease or condition occurrence. In further embodiments, the hyaluronidase is administered within about one day, two days, three days, four days, five days, six days up to seven days of the injury or traumatic event or disease or condition occurrence. In further embodiments, the hyaluronidase is administered about a week or more after injury or traumatic event or disease or condition has occurred. In further embodiments, the hyaluronidase is administered within about a month of the injury or traumatic event or disease or condition occurrence. In further embodiments, the hyaluronidase can be administered months after the injury or traumatic event or disease or condition has occurred. As shown herein, hyaluronidase reduced edema even in dead brain tissue, thus, there is no time limit as to when it would be effective in reducing edema in live brain tissue.

Additionally, hyaluronidase can be administered when edema in the brain tissue and/or intracranial pressure is known or suspected in a subject.

Because the hyaluronidase is administered to the brain to be effective and is not a compound that can cross the blood brain barrier, modes of administration that aid in delivery of the compound across the blood brain barrier must be used.

One mode of administration is intraventricular, through a surgically implanted drain or shunt. These types of devices are often implanted into the brains of patients who have suffered from TBI, or a stroke or had surgery, and hyaluronidase can be delivered via the drains or shunts. These devices can be connected to programmable pumps or other devices to deliver the hyaluronidase.

Other modes of administration include those that allow the hyaluronidase to cross the blood brain barrier and include but are not limited to loaded microbubble-enhanced focused ultrasound, receptor-mediated permabilitizer, nanoparticles, and liposomes. For review of methods of delivering drugs across the blood brain barrier, see generally Upadhyay, 2014.

Microbubbles are small "bubbles" of mono-lipids that normally do not have the ability to pass through the blood brain barrier. When combined with focused ultrasound, the bubbles reversibly open the blood brain barrier, allowing substances that are not normally permeable to enter the brain through the blood brain barrier. The ultrasound increases the permeability of the blood brain barrier by causing interference in the tight junctions in localized areas. This combined with the microbubbles allows for a very specific area of diffusion for the microbubbles, because they can only diffuse where the ultrasound is disrupting the barrier. The microbubble is loaded with an active drug to diffuse through the barrier and target a specific area. Studies have shown the effectiveness of this method for getting drugs to specific sites in the brain in animal models.

Receptor-mediated permabilitizers are drug compounds that increase the permeability of the blood brain barrier temporarily by increasing the osmotic pressure in the blood which loosens the tight junctions between the endothelial cells. By loosening the tight junctions normal injection of drugs intravenously can take place and effectively enter the brain.

Nanoparticles are nanoscale sized polymeric particles which are made up of natural or artificial polymers. These are ranging in size between about 10 and 1000 nm (1 mm). These interact with biological barriers and easily pass through them thus they are used for targeting of drugs and active agents. Drugs can be bound in form of a solid solution or dispersion or adsorbed to the surface or chemically attached on nanoparticles support carrier loading. Nanoparticle based delivery methods have proven to be one of the best methods to transfer drugs across the BBB.

There are two main categories of nanoparticles, inorganic and organic. Inorganic nanoparticles are mainly magnetic, metallic, nanoshells, and ceramic. Chitosan based nanoparticles are an example of a well-tolerated and effective inorganic nanoparticle. Organic nanoparticles include carbon nanotubes, quantum dots (semiconductors), dendrimers, and polymeric nanoparticles.

One promising compound for the nanoparticles is Human Serum Albumin (HSA). These nanoparticles have been shown to traverse the blood brain barrier carrying host drugs and are well tolerated. To further, to enhance the effectiveness of nanoparticles, these are coated with certain biodegradable materials which make them more permeable to cross the blood brain barrier.

Liposomes are widely used as carriers or delivery vehicles for therapeutic agents/drugs to send them at specific sites inside human body. These are vesicles of phospholipids that form spontaneously in solutions and are capable of trapping dissolved particles in solutions. Liposome technology has proved useful in crossing the blood brain barrier.

Further, advancements in liposomal drug delivery have produced long circulating and highly stable drug formulations. However, by making numerous improvements a number of liposome-based formulations are being made which effectively work as drug carriers. Liposomes are biodegradable liberating the charged molecules slowly when they degrade in the organism. Many of them are commercially available and some are in the developing phase and are undergoing clinical trials. These formulations can minimize systemic exposure, after transportation of drug and its biodistribution in target organs, cells, or compartments within the cells with or without expression of target recognition molecules on liposome membranes Liposomal drug delivery methods are widely used for brain tumor and antimicrobial therapeutics.

Colloidal drug carriers such as micellar solutions, vesicles, and liquid crystal dispersions can also be used to deliver drugs across the BBB.

Additional delivery systems currently being developed include exosomes and the use of viral vectors, such as AAV.

Additionally, hyaluronidase can be altered or modified in order for it to have the ability to cross the blood brain barrier by methods known in the art including but not limited to producing a prodrug or by peptide masking.

Prodrugs are bioreversible derivatives of drug molecules that undergo an enzymatic and/or chemical transformation in vivo to release the active parent drug. These are pharmacologically active agents that overcome barriers to a drug's usefulness. After delivery to the target site prodrugs exert desired pharmacological effect. More specifically inactive drugs or therapeutic compounds are made active by addition of lipophilic groups. These active forms of drug can cross the blood brain barrier. These are designed by using most common functional groups that may allow the drug permeability through the physical or any structural barrier device.

Similar to the idea of pro-drugs, another way of masking the drugs chemical composition is by masking a peptide's characteristics by combining with other molecular groups that are more likely to pass through the blood-brain barrier. An example of this is using a cholesteryl molecule instead of cholesterol that serves to conceal the water soluble characteristics of the drug. This type of masking aids in the drug traversing the blood brain barrier. It also can work to mask the drug peptide from peptide-degrading enzymes in the brain.

Selection of a therapeutically effective dose will be determined by the skilled artisan considering several factors, which will be known to one of ordinary skill in the art. Such factors include the particular form of the hyaluronidase, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

As shown in the Examples, the effects of one administration of hyaluronidase injection reduced edema with no adverse side effects such as disruption of the BBB or altered motor function, learning or memory. Thus, in some embodiments, hyaluronidase can be administered once.

Doses can be adjusted to optimize the effects in the subject. For example, hyaluronidase can be administered at a low dose to start and then increased over time to depending upon the subject's response. A subject can be monitored for improvement of their condition prior to changing, i.e., increasing or decreasing, the dosage. A subject can also be monitored for adverse effects prior to changing the dosage, i.e., increasing or decreasing, the dosage.

Thus, in other embodiments, hyaluronidase can be administered more than once. In some embodiments, hyaluronidase is administered once and then the subject is monitored for cerebral edema and/or intracranial pressure. If cerebral edema and/or intracranial pressure is still present, a subsequent dose of hyaluronidase is administered. These steps can be repeated as necessary.

A starting dose of hyaluronidase can be about 150 units to about 200 units in 1 ml. If a subsequent dose is needed, the same dose of about 150 units to about 200 units in 1 ml can be given or a higher or lower dose can be given.

Hyaluronidase is FDA approved and sold in the following strengths: 150 units; 1500 units; 150 units/ml; 200 units/ml; and 6200 units.

Kits

Also within the scope of the present disclosure are kits for practicing the method of the invention. Such kits may include hyaluronidase.

In some embodiments, the kit can comprise instructions for use in any of the methods described herein. The included instructions can comprise a description of administration of the agents to a subject to achieve the intended activity in a subject. The kit may further comprise a description of selecting a subject suitable for treatment based on identifying whether the subject is in need of the treatment.

The instructions relating to the use of the agents described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an intracranial shunt. A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

EXAMPLES

The present invention may be better understood by reference to the following non-limiting examples, which are presented in order to more fully illustrate the preferred embodiments of the invention. They should in no way be construed to limit the broad scope of the invention.

Example 1—Materials and Methods

Animals

Experimental animals were humanely housed and cared for under the supervision of the Institute of Comparative Medicine, and all experimental procedures were approved by the Institutional Animal Care and Use Committee at Columbia University. Three month-old male C57BL/6J mice (Jackson Laboratory, Bar Harbor, ME) were used for in vivo experiments, and brain tissue from 2-3 month-old male and female C57BL6 mice containing a nestin-δ-HSV TK-eGFP transgene (nestin-GFP mice) (Yu et al., 2008), bred at Columbia University Medical Center (CUMC), were used for in vitro experiments.

In Vitro Cortical Explant Swelling Assay

Following deep anesthetization with isoflurane and cervical dislocation, cortical tissues were dissected from naïve nestin-GFP mice, cut into quarters, weighed and then placed in 1 ml of Gey's solution (control) or 1 ml of Gey's solution containing 1 U/ml hyaluronidase (Type VI-S from bovine testes, Sigma Aldrich, St. Louis, MO). Explants were incubated for 2 hours at room temperature on a shaker before incubation at 37° C. for 22 hours. At 24 hours, samples were removed from solution and weighed again to obtain wet weight, and then dehydrated at 100° C. for 24 hours to obtain their dry weight. The percent water content was calculated as: % water content=[((wet weight)−(dry weight))/(wet weight)]×100.

Controlled Cortical Impact (CCI) Injury

A moderate contusion injury was imparted to the left parietal cortex of 3 month-old male C57B16 mice using a Leica One Stereotaxic Impact device (Leica, Houston, TX) as described previously (Blaiss et al., 2011) but with the following injury parameters: impact depth=1.0 mm, velocity=4.5 m/s, and dwell=0.3 s. Sham injury consisted of exposure to the same procedures without cortical impact. Briefly, mice received 5 mg/kg carprofen intraperitoneally (i.p.) and were anesthetized using 4% isoflurane in oxygen. Following aseptic procedure, the scalp was shaved, cleaned and 2 mg/kg bupivacaine administered subcutaneously before making a midline incision. A craniectomy was performed on the left parietal cortex exposing the dura, and then the CCI delivered.

Hyaluronidase Administration

Hyaluronidase (HA'ase) or vehicle (sterile PBS) was delivered 4 minutes after CCI or sham injury via stereotaxic intracerebroventricular (ICV) injection. For the injection, a second hole was drilled through the skull on the contralateral side, and a pulled glass pipette inserted at (−0.22, 1.0, 2.0 mm) to bregma. A total of 1 U of hyaluronidase in 10 µl in sterile PBS or vehicle (sterile PBS) was injected into the lateral ventricle at a rate of 1 µl/min. The pipette tip remained in place for 5 minutes before being withdrawn to minimize backflow. Following removal, the incision site was sutured, topical antibiotic was applied to the incision site, and the animal placed on a heating pad to recover.

Brain Water Content

Animals (n=4-5 per group) were euthanized 24 hours following injury via cervical dislocation following deep anesthesia. The brain was extracted and the hippocampi were collected by microdissection. The ipsilateral and contralateral hippocampus were immediately weighed to obtain wet weight. Samples were then dehydrated for 24 hours at 100° C. and weighed again to obtain dry weight. Percent water content was calculated as % water content=[((wet weight−(dry weight))/(wet weight)]×100.

1'9 dimethylmethylene blue (DMMB) colorimetric assay for GAG content Dehydrated explants and hippocampi samples were digested in 500 μl papain digestion solution (100 mM sodium phosphate, 10 mM EDTA, 10 mM cysteine, 125 μg/ml papain, pH 6.3) overnight at 60° C. To quantify GAG content, 40 μl of samples and standards (chondroitin-6-sulfate from shark cartilage, Sigma Aldrich) were mixed with 250 μl of DMMB dye (0.2% sodium formate, 0.2% formic acid, 0.001% DMMB, and 0.5% ethanol in distilled water, pH 3.5). Absorbance was measured at a primary wavelength of 595 nm with a reference wavelength of 540 nm. Values are expressed as μg GAG/mg dry weight.)

T2-Weighted MRI for Edema

Animals (n=4 per group) were imaged 24 hours following injury using a Bruker Biospec 94/20 9.4 Tesla magnetic resonance imager (MRI) (Bruker, Billerica, MA) at the Cancer Center Small Animal Imaging Shared Resource at Columbia University Medical Center's Herbert Irving Comprehensive Cancer Center. Animals were anesthetized using isoflurane, i.p. catheterized for injection and positioned in the magnet, where anesthesia was maintained, and heart rate was monitored throughout scanning T2-weighted images were obtained using 2D rapid acquisition with refocused echoes (RARE) with the following imaging parameters: pulse repetition time/echo time (TR/TE): 3300/44 ms; echo train: 8; number of excitations: 10; scan time: 13 m 12 s; matrix size: 256×196 pixels; spatial resolution: 86×86 μm voxels; slice thickness: 500 μm, no interslice gap.

Dynamic Contrast-Enhanced (DCE) T1-Weighted MRI for Blood Brain Barrier (BBB) Permeability Following the T2-weighted MRI imaging sequence, DCE T1-weighted MRI imaging was performed sequentially on the same animals without removal from the scanner or changing of alignment. Detection of a gadolinium-based contrast agent Gd-DTPA (Omniscan, GE Healthcare, Chicago, IL) over time was achieved using a 2D FLASH T1-weighted image sequence with the following parameters: TR/TE: 132.4/2.3 ms; number of excitations: 4; scan time: 76 s; matrix size: 256×196 pixels; spatial resolution: 86×86 μm voxels; slice thickness: 500 μm, no interslice gap; flip angle: 70°. The number of axial slices imaged of the brain ranged from 14-15 slices per animal, covering the top of the brain to the base of the neck to capture the carotid artery for determination of the arterial input function (AIF). 32 dynamic acquisitions were taken over a total period of 40 minutes. Following collection of pre-contrast images, a 300 ul bolus injection of Gd-DTPA was administered through the i.p. catheter for detection of BBB permeability by calculation of $K_{trans}$, the volume transfer coefficient of the Gd-DTPA from the vasculature to the extravascular extracellular space within the brain. Following imaging, animals were euthanized for measurement of brain % water content by the wet weight/dry weight method. Naïve, 3 month-old male C57B16 mice (n=4) were included for analysis of brain % water content to assess the effect of injury and treatment.

T2-Weighted Image Analysis for Edema Quantification

Edematous tissue appears hyperintense in T2-weighted MRI. To quantify the volume of edematous tissue, the ipsilateral hippocampus was first traced in serial images, (6-8 images per animal), using ImageJ (National Institutes of Health, Bethesda, MD). In each image, a circular region of interest (ROI) was placed in uninjured gray matter on the contralateral side to serve as a baseline tissue ROI. MRI images and traced ROIs were imported into MATLAB r2017a (MathWorks, Inc., Natick, MA), and a custom program was used to quantify hyperintense pixels in the ipsilateral hippocampus indicative of edema. Pixels were considered hyperintense if their intensity value was greater than 3 standard deviations from the mean intensity of the baseline tissue ROI. The percent edema in the hippocampus was calculated as the sum of the bright pixels in the ipsilateral hippocampus divided by the total number of pixels in the hippocampus.

T1-Weighted Image Analysis for Quantification of $K_{trans}$

Image analysis to calculate $K_{trans}$, indicative of BBB permeability, was performed using a custom MATLAB program and the hippocampal ROIs traced in the corresponding T2 images. For kinetic modelling, first-order unidirectional transport of Gd-DTPA across a semi-permeable BBB separating two compartments was assumed, described by the following differential equation:

$$\frac{dC_T(t)}{d} = K_{trans} \; C_A(t) \quad [1]$$

where $C_T(t)$ is the concentration of Gd-DTPA in the tissue compartment, $C_A(t)$ is the concentration in the arterial compartment (AIF), and $K_{trans}$ is the transfer coefficient. This is a modified version of the kinetic model described by Tofts and Kermode (Tofts and Kermode, 1991) in which the term accounting for tracer movement from the tissue compartment back to the arterial compartment is removed, assuming unidirectional transport at the early time points after injection of the current study.

Following Vlachos, showed that the time-course of the arterial tracer concentration (AIF) was modeled by a biexponential function (AIF):

$$\frac{dC_T(t)}{d} = K_{trans} \; C_A(t) \quad [2]$$

Substituting the expression in [2] for $C_A(t)$ in [1] and solving the resulting first-order linear differential equation for $C_T(t)$ yields the following analytical solution:

$$C_T(t) = K_{trans}\left[\frac{A_1}{m_1}(1 - e^{-m_1 t}) + \frac{A_2}{m_2}(1 - e^{-m_2 t})\right] + C_{T0} \quad [3]$$

where $C_{T0}$ is the initial value of $C_T(t)$.

Gd-DTPA concentration was determined from temporal changes in T1-weighted DCE-MRI signal intensities using the following expression (Vlachos et al., 2010):

$$C(n) = \frac{S(1) - S(n)}{S(1) \times r_1 \times T_{10}} \quad [4]$$

where n is acquisition number, $r_1$ is the T1 relaxivity of Gd-DTPA, and $T_{10}$ is the T1 relaxation time of the compartment (arterial blood or brain tissue). Vlachos et al. found the $r_1$ of Gd-DTPA to be 2.6 mM-1s-1 (Vlachos et al., 2010), and Thomas et al. found $T_{10}$ of arterial blood and brain tissue in mice to be 1.5 seconds and 0.9 seconds (Thomas et al., 2006), respectively. The average tracer concentration in an ROI at each time point was calculated from the averaged signal intensity of the ROI and [4].

AIF parameters (A1, A2, m1, and m2) were obtained by fitting the expression in [2] to tracer concentration in the carotid artery. $K_{trans}$ was determined by fitting expression [3] to the tracer concentration over time in a tissue region.

Behavioral Testing

Functional outcome was evaluated in a cohort of 3-month-old male C57BL/6J mice exposed to sham or CCI injury and treated with ICV injection of vehicle or hyaluronidase, as described above, using the rotarod task for motor deficits and the Morris water maze task for hippocampal-dependent spatial learning and memory. Naïve mice were included as a control group to detect any changes in behavior due to ICV injection. Prior to injury, 85 mice were acclimated to the rotarod (Rotarod/RS; Panlab/Harvard Apparatus; Barcelona, Spain) and baseline testing was performed to place mice into one of five experimental groups (naïve, sham vehicle, sham HA'ase, CCI vehicle, CCI HA'ase) so that the pre-injury baseline between groups was not significantly different. For all testing, 4 sequential trials were performed for each mouse, and average latency to fall was calculated from trials 2-4. The speed of the rotarod increased linearly from 4 to 40 rpm over the course of 60 s, the length of the trial. Animals were tested on the rotarod on days 3, 7 and 14 after injury (n=8-12 mice/group).

Animals were evaluated in the Morris water maze task at days 16-20 after injury (n=11-17/group). Spatial learning was evaluated on days 16-19 after injury by measuring the latency to find a 10 cm-diameter platform submerged 0.5 cm below the surface in a 120 cm-diameter circular pool of water using extramaze visual cues. Learning trials consisted of 4 trials a day for 4 days. Mice were placed into the pool at one of four entry quadrants and given 60 seconds to swim. If a mouse did not find the platform in 60 seconds, it was guided to and placed on the platform for 15 seconds. The pool water was maintained at 22-25° C. and made opaque using white paint. A video camera (Computar; Cary, NC) and ANY-maze behavioral tracking software (Stoelting Co., Wood Dale, IL) were used to detect the mouse's body and track and record swim path, distance travelled, mean speed and latency to the platform. The average latency to find the platform was calculated for each day from the four trials. A single probe trial for memory was conducted on day 5 of testing (day 20 after injury). The platform was removed, and the time spent in the target quadrant (the quadrant previously containing the platform) was recorded as well as the mean speed and distance travelled to assess swimming performance. Following the memory probe trial, a visible platform trial was conducted to rule out visual deficits. The platform was raised above the surface and flagged, and the latency to find the platform was recorded. Testing and data analyses were performed by an investigator blinded to group and treatment.

Statistical Analyses

Statistical analyses were performed using GraphPad Prism 7 (GraphPad Software, Inc., La Jolla, CA). The following statistical tests were used: Student's unpaired t-test for in vitro water content and DMMB data and in vivo MRI image analysis data; one-way ANOVA with Tukey's multiple comparisons post-hoc test for in vivo water content and DMMB data, in vivo MRI water content data, and Morris water maze percent time in target quadrant, mean speed and distance travelled data; and two-way repeated measures ANOVA with Tukey's multiple comparisons post hoc test for latency to fall off the rotarod and latency to find the platform in Morris water maze learning trials. Differences of $p<0.05$ were considered statistically significant. Values are presented graphically as mean with error bars for standard error, and in the text as mean±standard deviation.

Example 2—Hyaluronidase Reduced FCD and Water Uptake In Vitro

In cortical explants, hyaluronidase reduced water content (93.0±0.75 vs. 94.05±0.36; p<0.05; FIG. 1A) and GAG content (5.5 µg/mg±1.2 vs. 7.8 µg/mg±1.9; p<0.05; FIG. 1B) compared to control solution.

Example 3—Hyaluronidase Reduced CCI-Induced Hippocampal Edema

CCI increased the percent water content of the ipsilateral hippocampus in vehicle-treated mice (80.4±0.46) compared to sham mice treated with vehicle (77.37±0.48; p<0.001) and sham mice treated hyaluronidase (78.66±1.14; p<0.05). Treatment with hyaluronidase after CCI reduced edema compared to vehicle-treated CCI mice (78.15±0.65 vs. 80.4±0.46; p<0.01) so that the percent water content in hyaluronidase CCI mice was similar to sham mice (FIG. 1C). GAG content in the samples from the different groups of mice was not different (sham vehicle: 8.86 µg/mg±0.84; sham HA'ase: 8.47 µg/mg±2.79; CCI vehicle: 7.66 µg/mg±0.25; CCI HA'ase: 7.36 µg/mg±1.36; n.s.; FIG. 1D).

Figure 2B:
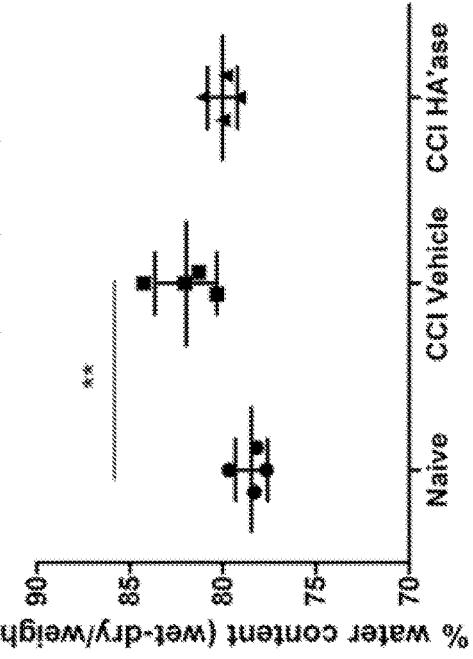
FIG. 2B is a graph quantifying and showing that the hyperintense pixels (edema volume measured by T2-weighted MRI) in the ipsilateral hippocampus were reduced in HA'ase-treated CCI mice compared to CCI mice treated with vehicle.
Figure 2D:
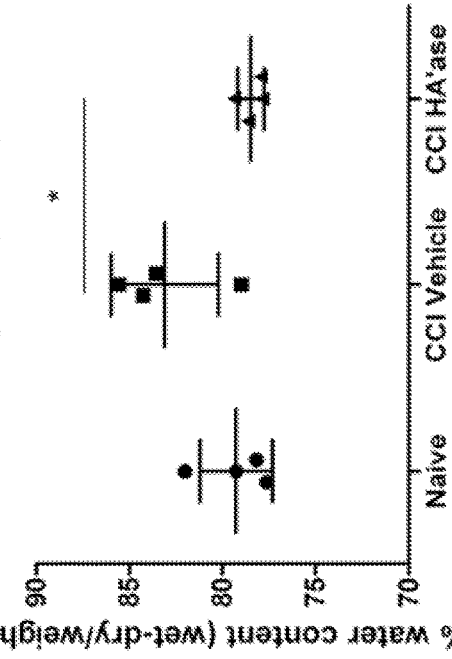
FIG. 2D is a graph quantifying and showing that the hyperintense pixels (edema volume measured by T2-weighted MRI) in the contralateral hippocampus were reduced in HA'ase-treated CCI mice compared to CCI mice treated with vehicle.
Figure 2C:
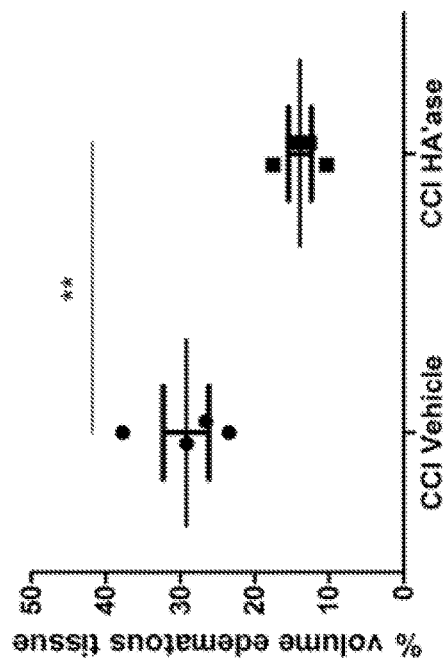
FIG. 2C is a graph showing the water content in CCI vehicle mice was elevated compared to CCI HA'ase mice in the ipsilateral hippocampus post-mortem as measured by wet-weight/dry-weight method.

Example 4—Hyaluronidase Reduced Post-Traumatic Brain Edema in Living Mice without Increasing BBB Permeability Hyaluronidase reduced the percentage of hyperintense, edematous pixels in the ipsilateral hippocampus 24 hours after CCI so that the percent volume of edematous tissue in hyaluronidase-treated CCI mice was less than half of that in vehicle-treated CCI mice as measured by T2-weighted MRI (13.88±3.1 vs. 29.23±6.14; p<0.01; FIGS. 2A and 2B). In the same animals, the percent water content of the ipsilateral hippocampus (as measured by wet-weight/dry-weight) in vehicle-treated CCI mice was increased compared to naïve mice (82.0±1.68 vs. 78.47±0.85; p<0.01), although the difference between hyaluronidase-treated CCI mice (80.03±0.80) and naïve mice was not statistically significant (FIG. 2C).

Figure 2E:
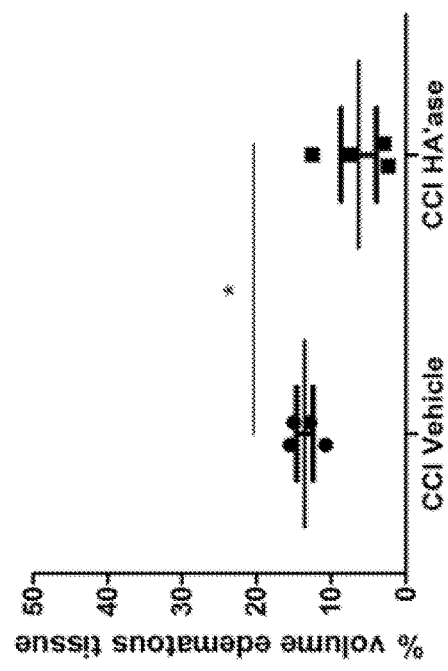
FIG. 2E a graph showing the water content in CCI vehicle mice was elevated compared to CCI HA'ase mice in the contralateral hippocampus post-mortem as measured by wet-weight/dry-weight method.

Edema in the contralateral hippocampus was significantly increased in vehicle-treated CCI mice but not hyaluronidase-treated CCI mice by both T2-weighted MRI (p<0.01; FIG. 2D) and the wet-weight/dry-weight method (p<0.05; FIG. 2E).

Figure 3A:
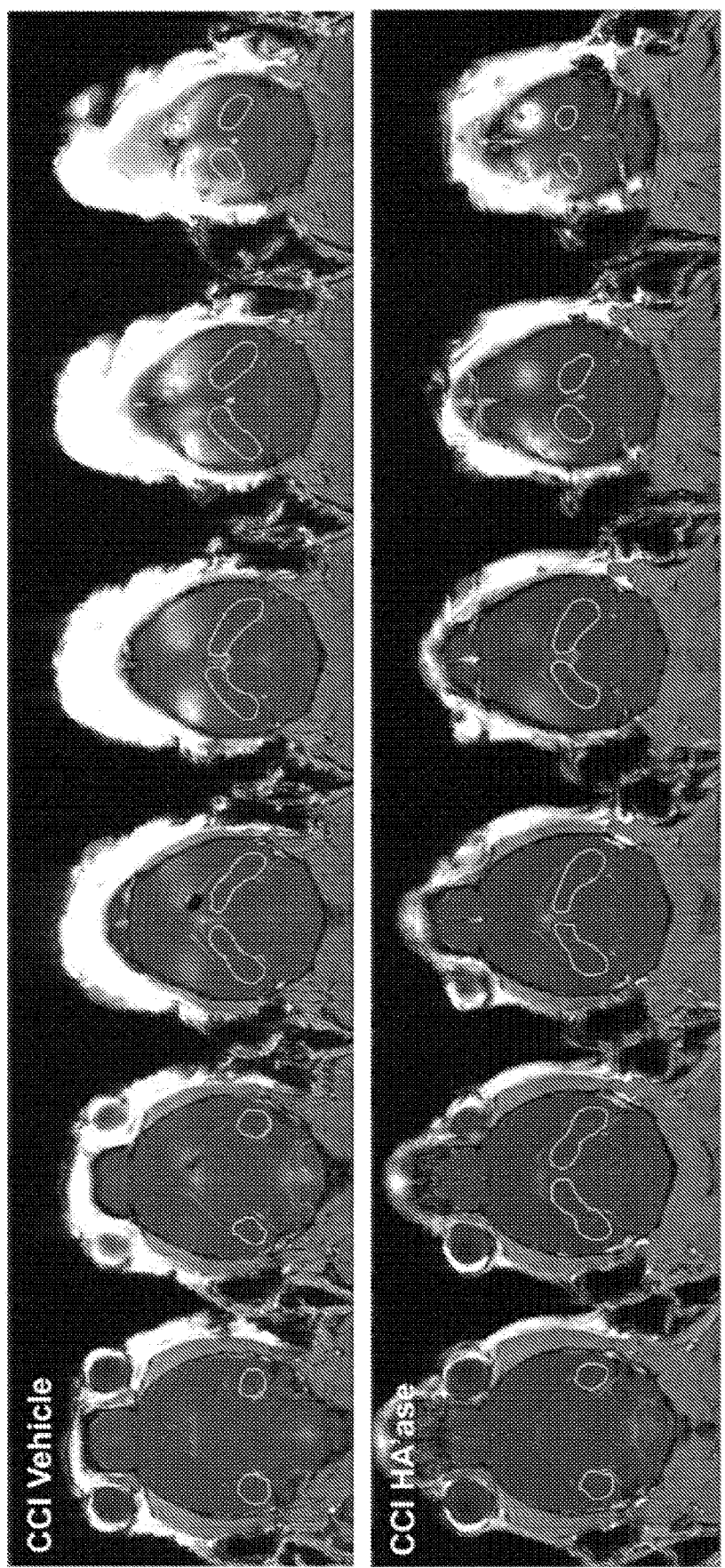
FIG. 3A are representative axial T1-weighted MRI images from CCI vehicle (top images) and CCI HA'ase (bottom images) mice showing extravasation of the contrast agent Gd-DTPA, which appears hyperintense, from the vasculature.

$K_{trans}$ did not differ between the ipsilateral hippocampus in vehicle- and hyaluronidase-treated CCI mice (0.00063±0.00041 vs. 0.00077±0.00078; n.s.; FIG. 3B). $K_{trans}$ values for the contralateral hippocampus were lower than that for the ipsilateral hippocampus in both groups but were not significantly different from each other (7.5e-5±0.00015 vs. 6.8e-5±0.00012; n.s; FIG. 3C).

Example 5—Hyaluronidase Treatment Did not Alter Recovery of Function in the Rotarod or Morris Water Maze Tasks After CCI Rotarod testing was performed as described in Example 1 on the five groups of mice: naïve; sham vehicle; sham HA'ase; CCI vehicle; and CCI HA'ase.

Figure 4A:
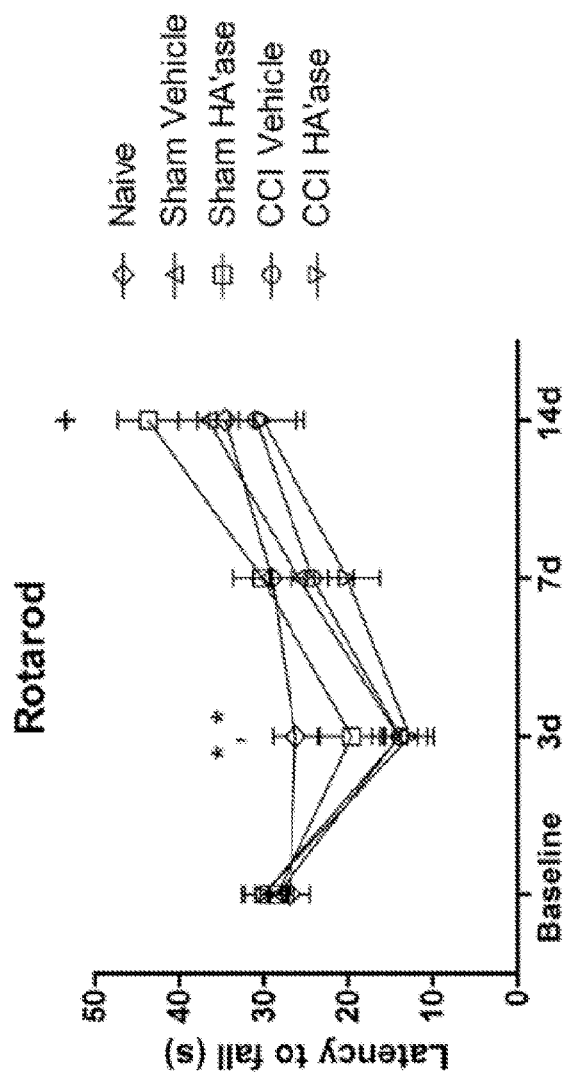
FIG. 4A is a graph showing the results of the rotarod task for five groups of mice: naïve (control); sham treated with vehicle; sham treated with HA'ase; CCI treated with vehicle; and CCI treated with HA'ase. Although performance on the rotarod task was significantly decreased at 3 days post-injury for sham vehicle and CCI HA'ase mice, all groups recovered to at least baseline performance by 14 days post-injury. $*p<0.05$ for sham vehicle and CCI HA'ase vs. naïve; $+p<0.05$ for sham HA'ase vs. CCI HA'ase; two-way repeated measures ANOVA with Tukey's post hoc multiple comparisons.

Two-way repeated-measures ANOVA with test day and group as the dependent variables found a significant main effect of test day ($F_{3,126}=51.4$, $p<0.001$) and a significant group x test day interaction ($F_{12,126}=2.95$, $p<0.01$), but the main effect of group was not significant ($F_{4,42}=1.4$, n.s.; FIG. 4A). Tukey's post hoc testing for simple effects found a reduction in latency to fall at 3 day post-injury for sham vehicle (14.0 s±6.7) and CCI hyaluronidase-treated mice (12.7 s±8.6) compared to naïve mice (26.3 s±8.1) ($p<0.05$). By day 14 after injury, the performance of all groups returned to or surpassed baseline, with sham vehicle-treated and hyaluronidase-treated mice performing significantly better than at baseline (43.7 s±11.0 vs. 28.4 s±5. 9; $p<0.001$), and better than CCI hyaluronidase-treated mice (43.7 s±11.0 vs.30.1 s±11.8; $p<0.05$).

Figure 4B:
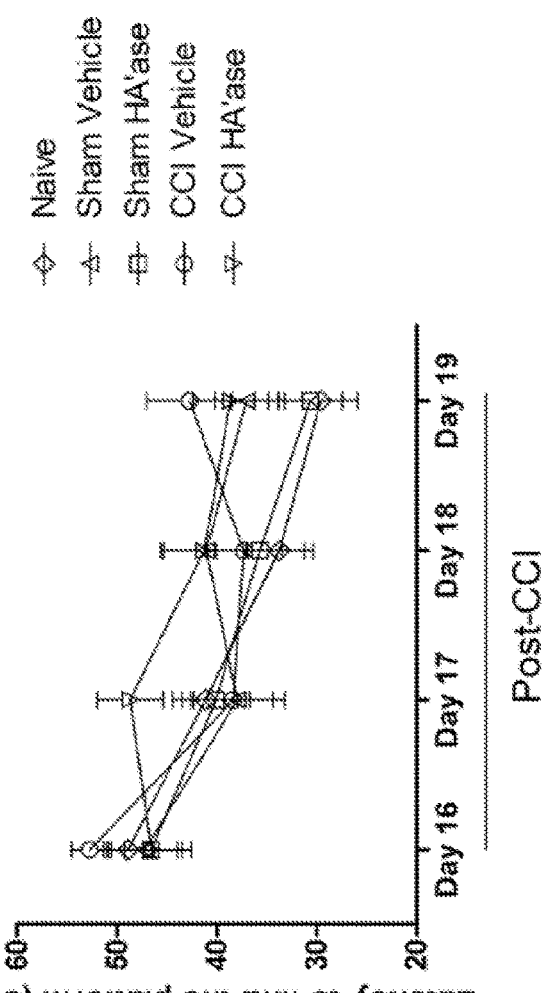
FIG. 4B is a graph showing the results of the Morris water maze learning trials for five groups of mice: naïve (control); sham treated with vehicle; sham treated with HA'ase; CCI treated with vehicle; and CCI treated with HA'ase. Overall, while the latency to find the platform in the Morris water maze decreased over training days in all groups, indicative of learning, there was no difference between groups (and two-way repeated measures ANOVA with Tukey's post hoc multiple comparisons).

Hippocampal-dependent spatial learning was evaluated on days 16-19 after injury. Two-way repeated-measures ANOVA with test day and group as the dependent variables found a significant main effect of test day ($F_{3,180}=15.5$, $p<0.001$), while the main effect of group was not significant ($F_{4,60}=1.1$, n.s.) nor was the group x test day interaction ($F_{12,180}=1.41$, n.s.; FIG. 4B).

Tukey's post hoc analysis comparing groups at different time points found no significant differences between any groups at any time point.

Memory was assessed in the Morris water maze task on day 20 after injury following conclusion of the learning trials as described in Example 1 on the five groups of mice: naïve; sham vehicle; sham HA'ase; CCI vehicle; and CCI HA'ase.

Figure 4C:
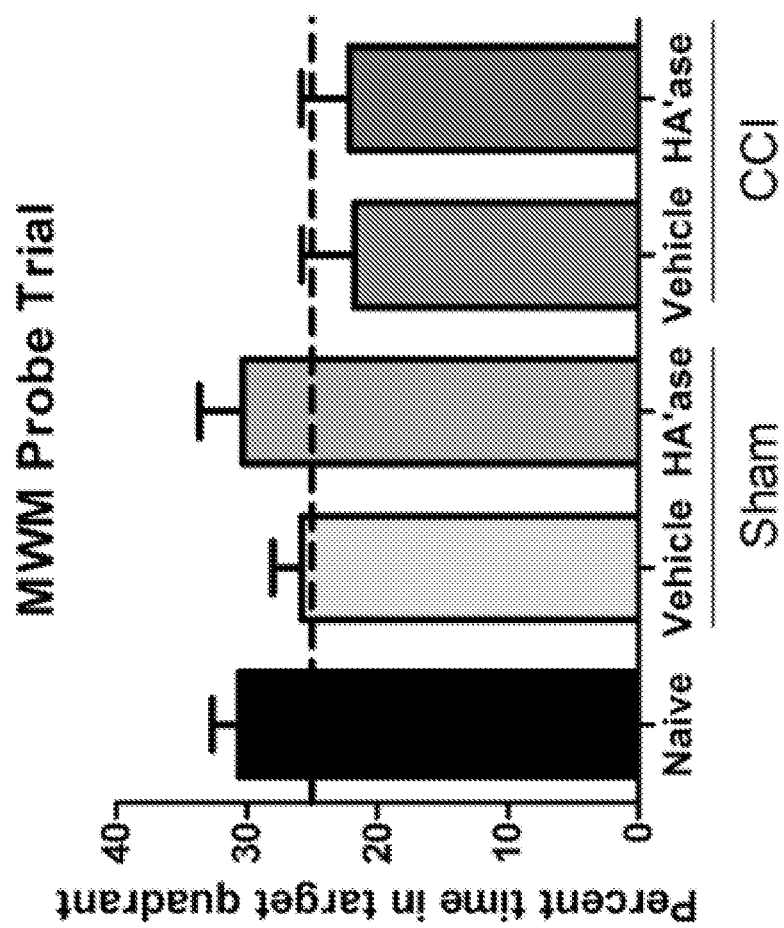
FIG. 4C shows that the results of the Morris water maze memory probe trial conducted on day 20 after injury for five groups of mice: naïve (control); sham treated with vehicle; sham treated with HA'ase; CCI treated with vehicle; and CCI treated with HA'ase. There was no difference between groups (n=11-17 mice/group) a one-way ANOVA with Tukey's post hoc multiple comparisons, n.s.).

There was no difference in time spent in the target quadrant between groups (naïve: 30.6±8.5; sham vehicle: 25.8±7.67; sham HA'ase: 30.3±11.38; CCI vehicle: 21.7±13.48; CCI HA'ase: 22.2±13.31; n.s.; FIG. 4C). Naïve and sham mice performed better than chance (25%), suggesting retention of the platform location. Deficits in motor and visual function were not observed, as all groups were comparable in mean speed (naïve: 0.18 m/s±0.04; sham vehicle: 0.17 m/s±0.03; sham HA'ase: 0.17 m/s±0.03; CCI vehicle: 0.15 m/s±0.06; CCI HA'ase: 0.15 m/s±0.05; n.s.) and distance travelled (naïve: 11.0 m±2.17; sham vehicle: 10.3 m±1.57; sham HA'ase: 10.2 m±1.55; CCI vehicle: 9.2 m±3.65; CCI HA'ase: 9.0 m±2.76; n.s.) during the memory probe trial, and all mice tested found the raised platform during the visible probe trial on the last day of testing.

These results show that treatment with hyaluronidase has no adverse effects to motor function, behavior and learning after recovery.

REFERENCES

Angeli and Stylianopoulos (2017) Experimental measurements and mathematical modeling towards quantification of brain swelling stress. Journal of Biomechanics 56:42-47.

Baskaya et al. (1997) The biphasic opening of the blood-brain barrier in the cortex and hippocampus after traumatic brain injury in rats. Neuroscience Letters 226:33-36.

Bhattacharya et al. (1989) Hyaluronan affects extravascular water in lungs of unanesthetized rabbits. Journal of Applied Physiology 66:2595-2599.

Blaiss et al. (2011) Temporally specified genetic ablation of neurogenesis impairs cognitive recovery following brain injury. Journal of Neuroscience 31:4906-16.

Chakraborty et al. (2016) Neuroprotection Trials in Traumatic Brain Injury. Current Neurology and Neuroscience Reports 16:29.

Donkin and Vink (2010) Mechanisms of cerebral edema in traumatic brain injury: therapeutic developments. Current Opinion in Neurology 23:293-299.

Elkin et al. (2010) Fixed negative charge and the Donnan effect: a description of the driving forces associated with brain tissue swelling and oedema. Philosophical Transactions Series A, Mathematical, Physical, and Engineering sciences 368:585-603.

Elkin et al. (2011) Chondroitinase ABC reduces brain tissue swelling in vitro. Journal of Neurotrauma 28:2277-2285.

Finan et al. (2016) Intracerebroventricular administration of chondroitinase ABC reduces acute edema after traumatic brain injury in mice. BMC Research Notes 9:160.

Hunger et al. (2012) Hydration dynamics of hyaluronan and dextran. Biophysical Journal 103:L10-12.

Hylin et al. (2013) Disruption of the perineuronal net in the hippocampus or medial prefrontal cortex impairs fear conditioning. Learning and Memory 20:267-273.

Kochlamazashvili et al. (2010) The extracellular matrix molecule hyaluronic acid regulates hippocampal synaptic plasticity by modulating postsynaptic L-type Ca(2+) channels. Neuron 67:116-128.

Lang et al. (2014) Is the Donnan effect sufficient to explain swelling in brain tissue slices? Journal of the Royal Society, Interface 11:20140123.

Marmarou et al. (2000) Contribution of edema and cerebral blood volume to traumatic brain swelling in head-injured patients. Journal of Neurosurgery 93:183-193.

Marmarou et al. (2006) Predominance of cellular edema in traumatic brain swelling in patients with severe head injuries. Journal of Neurosurgery 104:720-730.

Nettelbladt et al. (1989) Lung accumulation of hyaluronan parallels pulmonary edema in experimental alveolitis. The American Journal of Physiology 139:682-87.

Stocchetti and Maas (2014) Traumatic intracranial hypertension. The New England Journal of Medicine 370:2121-2130.

Stocchetti et al. (1999) Intracranial hypertension in head injury: management and results. Intensive care medicine 25:371-376.

Thomas et al. (2006) In vivo measurement of the longitudinal relaxation time of arterial blood (T1a) in the mouse using a pulsed arterial spin labeling approach. Magnetic Resonance in Medicine 55:943-947.

Tofts et al. (1991) Measurement of the blood-brain barrier permeability and leakage space using dynamic MR imaging. 1. Fundamental concepts. Magnetic Resonance in Medicine 17:357-367.

Toole (2004) Hyaluronan: from extracellular glue to pericellular cue. Nature Reviews: Cancer 4:528-539.

Tucker et al. (2017) Early Brain Edema is a Predictor of In-Hospital Mortality in Traumatic Brain Injury. The Journal of Emergency Medicine 53:18-29.

Upadhyay (2014) Drug delivery Systems, CNS Protection, and the Blood Brain Barrier. BioMed Research International 2014: ID 869269

Vlachos et al. (2010) Permeability assessment of the focused ultrasound-induced blood-brain barrier opening using dynamic contrast-enhanced MRI. Physics in Medicine and Biology 55:5451-5466.

Waldenstrom et al. (1991) Accumulation of hyaluronan and tissue edema in experimental myocardial infarction. The Journal of Clinical Investigation 88:1622-1628.

Winkler et al. (2016) Cerebral Edema in Traumatic Brain Injury: Pathophysiology and Prospective Therapeutic Targets. Neurosurgery Clinics of North America 27:473-488.

Yu et al. (2008) Traumatic brain injury-induced hippocampal neurogenesis requires activation of early nestin-expressing progenitors. The Journal of Neuroscience: the Official Journal of the Society for Neuroscience 28:12901-12912.

Zweckberger et al. (2006) Effect of early and delayed decompressive craniectomy on secondary brain damage after controlled cortical impact in mice. Journal of Neurotrauma 23:1083-1093.

The invention claimed is:

1. A method of treating, preventing, reducing and/or abolishing cerebral edema and/or intracranial pressure in a subject in need thereof, the method comprising administering to the subject a therapeutically effective amount of hyaluronidase, wherein the edema is a result of traumatic brain injury, stroke, brain tumor, and post-operative swelling, wherein the hyaluronidase is administered intravenously to the subject after the traumatic brain injury, stroke, brain tumor, or post-operative swelling, wherein the hyaluronidase is administered to the subject within about two days to within about a month of the traumatic brain injury, stroke, brain tumor, and post-operative swelling, and wherein the hyaluronidase crosses the blood brain barrier.

2. The method of claim 1, comprising administering the hyaluronidase immediately after the traumatic brain injury, stroke, brain tumor, or post-operative swelling.

3. The method of claim 1, comprising administering the hyaluronidase to the subject within about an hour to within about 24 hours of the traumatic brain injury, stroke, brain tumor, and post-operative swelling.

4. A method of treating, preventing, reducing and/or abolishing cerebral edema and/or intracranial pressure in a subject in need thereof, the method comprising administering to the subject a therapeutically effective amount of hyaluronidase, wherein the edema is a result of traumatic brain injury, stroke, brain tumor, and post-operative swelling, wherein the hyaluronidase is administered intravenously to the subject after the traumatic brain injury, stroke, brain tumor, or post-operative swelling, wherein the hyaluronidase is administered to the subject after a month of the traumatic brain injury, stroke, brain tumor, and post-operative swelling, and wherein the hyaluronidase crosses the blood brain barrier.

5. The method of claim 1, comprising administering the hyaluronidase to the subject as soon as the cerebral edema and/or intracranial pressure is known or suspected.

6. A method of treating, preventing, reducing and/or abolishing cerebral edema and/or intracranial pressure in a subject in need thereof, the method comprising administering to the subject a therapeutically effective amount of hyaluronidase, wherein the edema is a result of traumatic brain injury, stroke, brain tumor, and post-operative swelling, wherein the hyaluronidase is administered to the subject after the traumatic brain injury, stroke, brain tumor, or post-operative swelling and by a method that allows the hyaluronidase to cross the blood brain barrier, wherein the hyaluronidase is administered to the subject within about two days to within about a month of the traumatic brain injury, stroke, brain tumor, and post-operative swelling,
wherein the therapeutically effective amount of hyaluronidase is about 150 to about 200 units in 1 ml.

7. The method of claim 6, comprising administering the hyaluronidase immediately after the traumatic brain injury, stroke, brain tumor, or post-operative swelling.

8. The method of claim 6, comprising administering the hyaluronidase to the subject within about an hour to within about 24 hours of the traumatic brain injury, stroke, brain tumor, and post-operative swelling.

9. A method of treating, preventing, reducing and/or abolishing cerebral edema and/or intracranial pressure in a subject in need thereof, the method comprising administering to the subject a therapeutically effective amount of hyaluronidase, wherein the edema is a result of traumatic brain injury, stroke, brain tumor, and post-operative swelling, wherein the hyaluronidase is administered to the subject after the traumatic brain injury, stroke, brain tumor, or post-operative swelling and by a method that allows the hyaluronidase to cross the blood brain barrier,
wherein the therapeutically effective amount of hyaluronidase is about 150 to about 200 units in 1 ml, and wherein the hyaluronidase is administered to the subject after a month of the traumatic brain injury, stroke, brain tumor, and post-operative swelling.

10. The method of claim 6, comprising administering the hyaluronidase to the subject as soon as the cerebral edema and/or intracranial pressure is known or suspected.

11. A method of treating, preventing, reducing and/or abolishing cerebral edema and/or intracranial pressure in a subject in need thereof, the method comprising administering to the subject a therapeutically effective amount of hyaluronidase, wherein the edema is a result of traumatic brain injury, stroke, brain tumor, and post-operative swelling, wherein the hyaluronidase is administered to the subject after the traumatic brain injury, stroke, brain tumor, or post-operative swelling and by a method that allows the hyaluronidase to cross the blood brain barrier,
wherein the therapeutically effective amount of hyaluronidase is about 150 to about 200 units in 1 ml, wherein the method that allows the hyaluronidase to cross the blood brain barrier is chosen from the group consisting of loaded microbubble-enhanced focused ultrasound, receptor-mediated permeabilizer, nanoparticles, and liposomes.

12. A method of treating, preventing, reducing and/or abolishing cerebral edema and/or intracranial pressure in a subject in need thereof, the method comprising administering to the subject a therapeutically effective amount of hyaluronidase, wherein the edema is a result of traumatic brain injury, stroke, brain tumor, and post-operative swelling, wherein the hyaluronidase is administered to the subject after the traumatic brain injury, stroke, brain tumor, or post-operative swelling and by a method that allows the hyaluronidase to cross the blood brain barrier, wherein the method that allows the hyaluronidase to cross the blood brain barrier is chosen from the group consisting of loaded microbubble-enhanced focused ultrasound, receptor-mediated permeabilizer, nanoparticles, and liposomes,
wherein the therapeutically effective amount of hyaluronidase is about 150 to about 6200 units.

13. A method of treating, preventing, reducing and/or abolishing cerebral edema and/or intracranial pressure in a subject in need thereof, the method comprising administering to the subject a therapeutically effective amount of hyaluronidase, wherein the edema is a result of traumatic brain injury, stroke, brain tumor, and post-operative swelling, wherein the hyaluronidase is administered by intracerebroventricular (ICV) injection to the subject after the traumatic brain injury, stroke, brain tumor, or post-operative swelling and wherein the hyaluronidase crosses the blood brain barrier,
 wherein the therapeutically effective amount of hyaluronidase is about 150 to about 6200 units.

14. The method of claim 13, wherein the therapeutically effective amount of hyaluronidase is about 150 to about 200 units.

15. The method of claim 1, wherein the hyaluronidase is administered to the subject within about 24 hours of the traumatic brain injury, stroke, brain tumor, and post-operative swelling.

16. The method of claim 6, wherein the hyaluronidase is administered to the subject within about 24 hours of the traumatic brain injury, stroke, brain tumor, and post-operative swelling.

* * * * *